US009211152B2

(12) United States Patent
Zalenski et al.

(10) Patent No.: US 9,211,152 B2
(45) Date of Patent: Dec. 15, 2015

(54) BONE PLATE HOLDER

(71) Applicant: Depuy Synthes Products, LLC, Raynham, MA (US)

(72) Inventors: Edward B. Zalenski, Raynham, MA (US); Michael D. Sorrenti, Raynham, MA (US); Thomas Gamache, Raynham, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 14/505,963

(22) Filed: Oct. 3, 2014

(65) Prior Publication Data
US 2015/0025582 A1    Jan. 22, 2015

Related U.S. Application Data

(60) Continuation of application No. 13/857,309, filed on Apr. 5, 2013, now Pat. No. 8,926,616, which is a division of application No. 12/835,969, filed on Jul. 14, 2010, now Pat. No. 8,425,520, which is a continuation-in-part of application No. 12/609,265, filed on Oct. 30, 2009, now abandoned.

(51) Int. Cl.
*A61B 17/88*    (2006.01)
*A61B 17/70*    (2006.01)
(Continued)

(52) U.S. Cl.
CPC ............. *A61B 17/88* (2013.01); *A61B 17/7071* (2013.01); *A61B 17/7074* (2013.01);
(Continued)

(58) Field of Classification Search
CPC ........... A61B 17/1728; A61B 17/1757; A61B 17/56; A61B 2017/564; A61B 17/70; A61B 17/7071; A61B 17/7074; A61B 17/80; A61B 17/808; A61B 17/88; A61B 17/8872; Y10S 606/914; Y10S 606/915
USPC .......... 606/71, 86 B, 86 R, 96, 101, 205–209, 606/280, 282, 903–906, 915
See application file for complete search history.

(56) References Cited

U.S. PATENT DOCUMENTS 1,985,108 A * 12/1934 Rush ........................... 606/86 R
3,727,611 A *  4/1973 Schultz ........................ 606/96
(Continued)

FOREIGN PATENT DOCUMENTS

EP            0599640       8/1998
WO         WO 9511632     5/1995
(Continued)

OTHER PUBLICATIONS

Frank, A Technique for Cervical Laminoplasty Using Mini Plates, British Journal of Neurosurgery, 1994, vol. 8, pp. 197-199.
Stanescue, "Morphometic Evaluation of the Cervico-Thoracic Junction, Practical Considerations for Posterior Fixation of the Spine", Spine, vol. 19, No. 18, 1994, pp. 2082-2088, J.B. Lippincott Co.

*Primary Examiner* — Larry E Waggle, Jr.
(74) *Attorney, Agent, or Firm* — Raymond N. Scott, Jr.

(57) ABSTRACT

An instrument for holding a bone plate may include a first arm, a second arm connected to and adjustable relative to the first arm, a first connection tip at the distal end of the first arm configured to connect to the first side wall of the bone plate, and a second connection tip at the distal end of the second arm configured to connect to the second side wall of the bone plate. A stabilizing member is connected to the first connection tip. The stabilizing member is distally spaced apart from the first connection tip to form an opening for receiving a portion of bone between the first connection tip and the stabilizing member.

7 Claims, 16 Drawing Sheets

(51) Int. Cl.
*A61B 17/80* (2006.01)
*A61B 17/56* (2006.01)
*A61B 17/17* (2006.01)

(52) U.S. Cl.
CPC .......... *A61B17/808* (2013.01); *A61B 17/8872* (2013.01); *A61B 17/1728* (2013.01); *A61B 17/1757* (2013.01); *A61B 2017/564* (2013.01); *Y10S 606/915* (2013.01)

(56) References Cited

U.S. PATENT DOCUMENTS

| | | | |
|---|---|---|---|
| 4,972,949 A | 11/1990 | Peiffer | |
| 5,085,660 A | 2/1992 | Lin | |
| 5,133,735 A | 7/1992 | Slater | |
| 5,133,736 A | 7/1992 | Bales, Jr. | |
| 5,141,519 A | 8/1992 | Smith | |
| 5,147,360 A | 9/1992 | Dubousset | |
| 5,147,378 A | 9/1992 | Markham | |
| 5,152,778 A | 10/1992 | Bales, Jr. | |
| 5,152,780 A | 10/1992 | Honkanen | |
| 5,176,702 A | 1/1993 | Bales | |
| 5,192,298 A | 3/1993 | Smith | |
| 5,199,566 A | 4/1993 | Ortiz | |
| 5,290,299 A | 3/1994 | Fain | |
| 5,336,228 A | 8/1994 | Cholhan | |
| 5,366,455 A | 11/1994 | Dove | |
| 5,380,324 A | 1/1995 | Muller | |
| 5,411,522 A | 5/1995 | Trott | |
| 5,423,826 A | 6/1995 | Coates | |
| 5,466,243 A | 11/1995 | Schmieding | |
| 5,470,333 A | 11/1995 | Ray | |
| 5,487,741 A | 1/1996 | Maruyama | |
| 5,498,263 A | 3/1996 | DiNello | |
| 5,501,683 A | 3/1996 | Trott | |
| 5,507,747 A | 4/1996 | Yuan | |
| 5,527,312 A | 6/1996 | Ray | |
| 5,531,745 A | 7/1996 | Ray | |
| 5,558,674 A | 9/1996 | Heggeness | |
| 5,616,144 A | 4/1997 | Yapp | |
| 5,637,112 A | 6/1997 | Moore | |
| 5,704,936 A | 1/1998 | Mazel | |
| 5,722,976 A | 3/1998 | Brown | |
| 5,735,852 A | 4/1998 | Amrein | |
| 5,735,899 A | 4/1998 | Schwartz | |
| 5,746,743 A * | 5/1998 | Greenberg | 606/96 |
| 5,830,231 A | 11/1998 | Geiges, Jr. | |
| 5,922,008 A | 7/1999 | Gimpelson | |
| 5,951,557 A | 9/1999 | Luter | |
| 5,961,530 A | 10/1999 | Moore | |
| 5,993,449 A | 11/1999 | Schlapfer | |
| 6,080,157 A | 6/2000 | Cathro | |
| 6,136,002 A | 10/2000 | Shih | |
| 6,273,253 B1 | 8/2001 | Forster | |
| 6,287,307 B1 | 9/2001 | Abboudi | |
| 6,325,625 B1 | 12/2001 | Meyer | |
| 6,355,038 B1 | 3/2002 | Pisharodi | |
| 6,440,135 B2 | 8/2002 | Orbay | |
| 6,458,131 B1 | 10/2002 | Ray | |
| 6,460,700 B2 | 10/2002 | Weisshaupt | |
| 6,530,933 B1 | 3/2003 | Yeung | |
| 6,572,617 B1 | 6/2003 | Senegas | |
| 6,610,091 B1 | 8/2003 | Reiley | |
| 6,626,909 B2 | 9/2003 | Chin | |
| 6,626,916 B1 | 9/2003 | Yeung | |
| 6,626,929 B1 | 9/2003 | Bannerman | |
| 6,635,087 B2 | 10/2003 | Angelucci | |
| 6,652,527 B2 | 11/2003 | Zucherman | |
| 6,660,007 B2 | 12/2003 | Khanna | |
| 6,663,654 B1 | 12/2003 | Husain | |
| 6,669,697 B1 | 12/2003 | Pisharodi | |
| 6,712,820 B2 | 3/2004 | Orbay | |
| 6,719,795 B1 | 4/2004 | Cornwall | |
| 6,767,351 B2 | 7/2004 | Orbay | |
| 6,811,567 B2 | 11/2004 | Reiley | |
| 6,880,699 B2 | 4/2005 | Gallagher | |
| 6,974,478 B2 | 12/2005 | Reiley | |
| 6,981,990 B2 | 1/2006 | Keller | |
| 6,997,953 B2 | 2/2006 | Chung | |
| 7,074,239 B1 | 7/2006 | Cornwall | |
| 7,087,084 B2 | 8/2006 | Reiley | |
| 7,090,676 B2 | 8/2006 | Huebner | |
| 7,201,751 B2 | 4/2007 | Zucherman | |
| 7,264,620 B2 | 9/2007 | Taylor | |
| 7,320,689 B2 | 1/2008 | Keller | |
| 7,344,537 B1 | 3/2008 | Mueller | |
| 7,452,368 B2 | 11/2008 | Liberatore | |
| 7,569,067 B2 | 8/2009 | Keller | |
| 7,625,376 B2 | 12/2009 | Brumfield | |
| 7,744,598 B2 | 6/2010 | Brumfield | |
| 8,425,515 B2 | 4/2013 | Gamache et al. | |
| 8,425,520 B2 | 4/2013 | Zalenski et al. | |
| 8,470,003 B2 | 6/2013 | Voellmicke et al. | |
| 2002/0017472 A1 | 2/2002 | Weisshaupt | |
| 2002/0029039 A1 | 3/2002 | Zucherman | |
| 2002/0046961 A1 | 4/2002 | Levinson | |
| 2002/0120335 A1 | 8/2002 | Angelucci | |
| 2002/0128682 A1 | 9/2002 | Prestel | |
| 2003/0045935 A1 | 3/2003 | Angelucci | |
| 2003/0045936 A1 | 3/2003 | Angelucci | |
| 2003/0125738 A1 | 7/2003 | Khanna | |
| 2004/0030388 A1 | 2/2004 | Null | |
| 2004/0102775 A1 | 5/2004 | Huebner | |
| 2004/0106927 A1 | 6/2004 | Ruffner | |
| 2004/0162558 A1 | 8/2004 | Hegde | |
| 2004/0210222 A1 | 10/2004 | Angelucci | |
| 2005/0038436 A1 | 2/2005 | Michelson | |
| 2005/0085818 A1 | 4/2005 | Huebner | |
| 2005/0107877 A1 | 5/2005 | Blain | |
| 2005/0119657 A1 | 6/2005 | Goldsmith | |
| 2005/0131412 A1 | 6/2005 | Olevsky | |
| 2005/0149021 A1 | 7/2005 | Tozzi | |
| 2005/0182407 A1 | 8/2005 | Dalton | |
| 2005/0234765 A1 | 10/2005 | Blumberg | |
| 2005/0251138 A1 | 11/2005 | Boris | |
| 2005/0273100 A1 | 12/2005 | Taylor | |
| 2006/0064091 A1 | 3/2006 | Ludwig et al. | |
| 2006/0079931 A1 | 4/2006 | Brennan et al. | |
| 2006/0190033 A1 | 8/2006 | Molloy | |
| 2006/0247635 A1 | 11/2006 | Gordon | |
| 2007/0123869 A1 | 5/2007 | Chin | |
| 2007/0219582 A1 | 9/2007 | Brunelle | |
| 2007/0276376 A1 | 11/2007 | Link | |
| 2008/0009865 A1 | 1/2008 | Taylor | |
| 2008/0183217 A1 | 7/2008 | Glaser | |
| 2008/0215096 A1 | 9/2008 | Nash | |
| 2008/0302688 A1 | 12/2008 | Iaconi-Forrer | |
| 2010/0016900 A1 | 1/2010 | Terres | |
| 2010/0057127 A1 | 3/2010 | McGuire | |
| 2011/0106083 A1 | 5/2011 | Voellmicke | |
| 2011/0106084 A1 | 5/2011 | Gamache | |
| 2011/0106087 A1 | 5/2011 | Gamache | |
| 2011/0106169 A1 | 5/2011 | Zalenski | |

FOREIGN PATENT DOCUMENTS

| | | |
|---|---|---|
| WO | WO 9512356 | 5/1995 |
| WO | WO 9605778 | 2/1996 |
| WO | WO 9709940 | 3/1997 |
| WO | WO 9937221 | 7/1999 |
| WO | WO 0044290 | 8/2000 |
| WO | WO 03007826 | 1/2003 |
| WO | WO 03020142 | 3/2003 |
| WO | WO 03101319 A3 | 1/2004 |
| WO | WO 2005096969 | 10/2005 |
| WO | WO 2005041752 A3 | 5/2006 |
| WO | WO 2006104487 | 10/2006 |
| WO | WO 2007127918 | 11/2007 |
| WO | WO 2011040983 | 4/2011 |

* cited by examiner

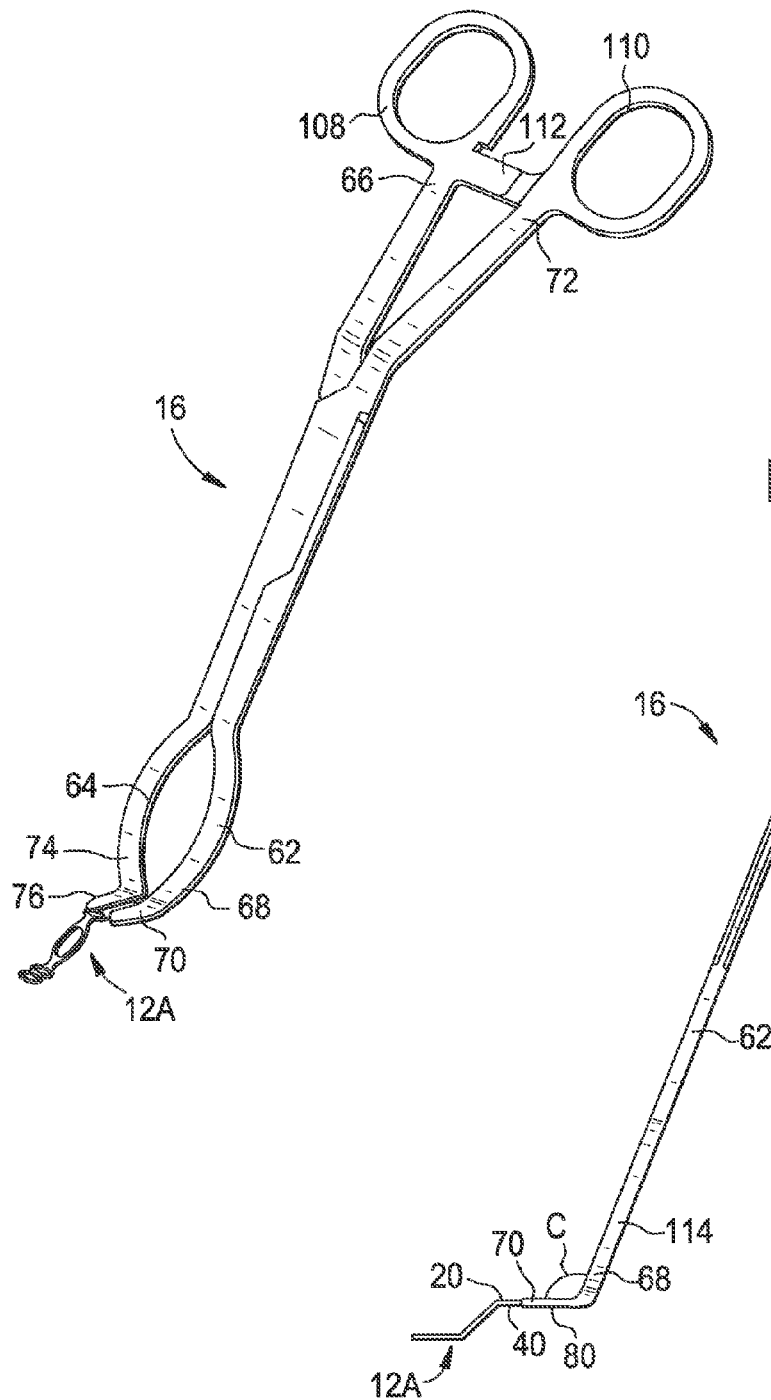

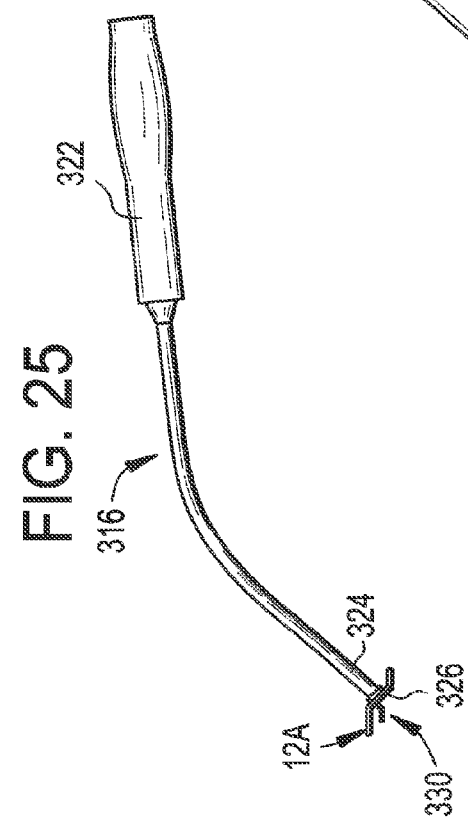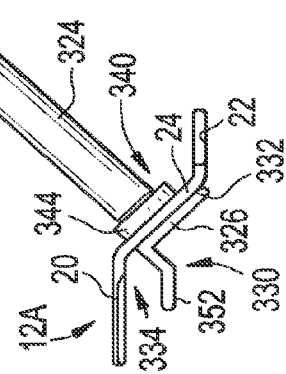

BONE PLATE HOLDER

CROSS REFERENCE TO RELATED APPLICATIONS

This application is a continuation of U.S. patent application Ser. No. 13/857,309, filed Apr. 5, 2013, pending, which is a divisional of U.S. patent application Ser. No. 12/835,969, filed Jul. 14, 2010, issued Apr. 23, 2013 as U.S. Pat. No. 8,425,520, which is a continuation-in-part of U.S. patent application Ser. No. 12/609,265, filed Oct. 30, 2009, abandoned. Each of the aforementioned patent applications is incorporated herein by reference.

BACKGROUND

In many spinal and orthopedic procedures a bone plate is used to fix bone segments, such as adjacent vertebrae. In laminoplasty procedures, for example, in which the lamina of a vertebra is cut and spaced apart to expand the spinal canal, a laminoplasty plate is frequently used to stabilize the cut vertebra after expansion of the spinal canal. Manipulating the laminoplasty plate into the proper position and anchoring it to the vertebra can be challenging, as laminoplasty plates are small and difficult to handle. For this reason, there is a need for improved instruments and techniques for manipulating laminoplasty plates and other types of bone plates.

SUMMARY

Disclosed herein are bone plate systems including a plurality of bone plates of differing lengths, such as a laminoplasty system having a plurality of laminoplasty plates of differing lengths, and an instrument for holding one of the bone plates. The instrument is particularly suited for manipulating bone plates into position relative to one or more bone segments and maintaining the bone plate in position as the bone plate is anchored to the bone segment.

In one aspect, an instrument for holding a bone plate may include a first arm having a proximal end and a distal end, a second arm connected to and adjustable relative to the first arm, a first connection tip at the distal end of the first arm configured to connect to the first side wall of the bone plate, and a second connection tip at the distal end of the second arm configured to connect to the second side wall of the bone plate. The instrument further includes a stabilizing member connected to the first connection tip. The stabilizing member is distally spaced apart from the first connection tip to form an opening for receiving a portion of bone between the first connection tip and the stabilizing member.

In another aspect, an instrument for holding a bone plate includes a shaft having a proximal handle and a distal end, a plate holding member connected to the distal end of the shaft and defining a proximal surface for receiving a first plate segment of the bone plate, and a stabilizing member connected to the plate holding member. The stabilizing member is distally spaced apart from the plate holding member to form an opening for receiving a portion of bone between the stabilizing member and a second plate segment of the bone plate when the first plate segment is positioned on the proximal surface of the plate holding member.

BRIEF DESCRIPTION OF THE FIGURES

These and other features and advantages of the devices and methods disclosed herein will be more fully understood by reference to the following detailed description in conjunction with the attached drawings in which like reference numerals refer to like elements through the different views. The drawings illustrate principles of the devices and methods disclosed herein and, although not to scale, show relative dimensions.

FIG. 7 is a perspective view of an instrument for holding a bone plate, illustrating the instrument holding a bone plate, FIG. 8 is a side view of the instrument of FIG. 7, FIGS. 25 and 26 are perspective views of another exemplary embodiment of an instrument for holding a bone plate, illustrating the instrument holding a bone plate.

DETAIL DESCRIPTION OF EXEMPLARY EMBODIMENTS

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The articles "a" and "an" are used herein to refer to one or to more than one (i.e. to at least one) of the grammatical object of the article. By way of example, "an element" means one element or more than one element.

The terms "comprise," "include," and "have," and the derivatives thereof, are used herein interchangeably as comprehensive, open-ended terms. For example, use of "comprising," "including," or "having" means that whatever element is comprised, had, or included, is not the only element encompassed by the subject of the clause that contains the verb.

Figure 1:
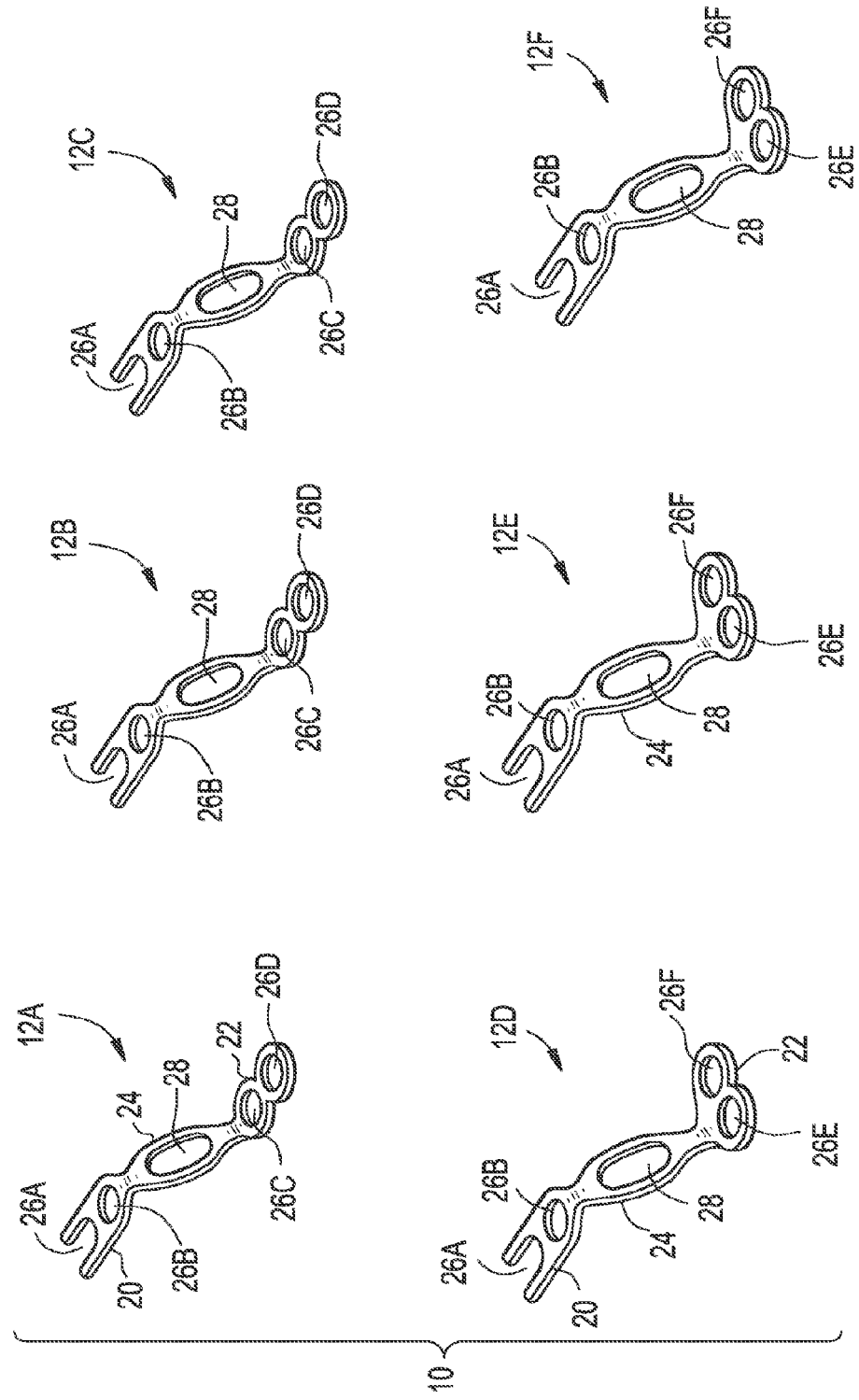
FIG. 1 is a perspective view of a laminoplasty system including a plurality of bone plates.
Figure 6:
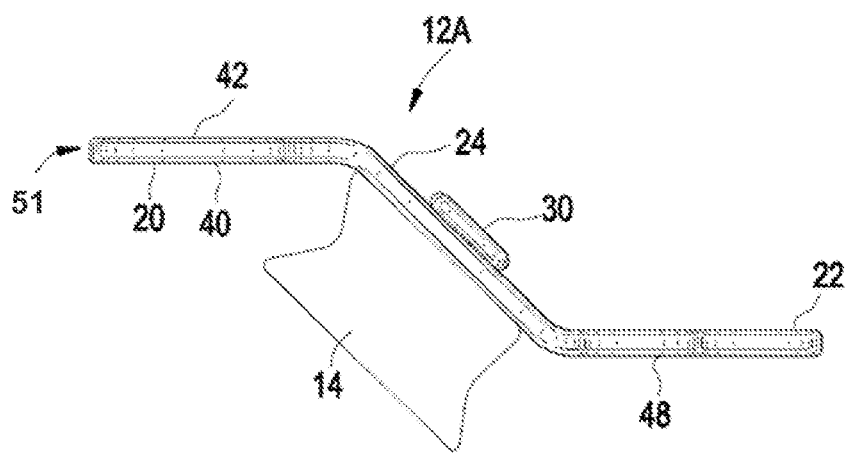
FIG. 6 is a side view of a bone plate and a bone graft of the laminoplasty of FIG. 1, illustrating the bone graft connected to the bone plate.

FIG. 1 illustrates an exemplary laminoplasty system 10 including a set of bone plates 12. The exemplary bone plates 12 are particularly suited for use in a surgical procedure to alleviate spinal cord compression by expanding the spinal canal, typically by displacing bone, such as the lamina, that surrounds the spinal cord. This procedure, generally referred to as laminoplasty, typically involves making two types of cuts into the lamina, a complete osteotomy through the lamina on one side of the spine and a partial osteotomy, or "green stick", on the contra-lateral lamina, which preserves the bottom cortex and creates a flexible hinge in the bone. This bridge of lamina bone is then levered open about the hinge and fixed with one of the plates 12 and a plurality of screws. In some procedures, a bone graft may be connected to the bone plate and positioned in the expanded lamina, typically between the cut lamina and the lateral mass of the vertebra, to facilitate fusion of the lamina to the lateral mass. The exemplary laminoplasty system 10, thus, also may include a plurality of bone grafts of differing length. Exemplary laminoplasty plates, bone grafts, and methods of expanding the spinal canal of a vertebra are described in commonly owned, co-pending U.S. patent application Ser. No. 12/609,251, filed Oct. 30, 2009, which is incorporated herein by reference. Typically, a bone graft 14 is connected to the bone plate 12 prior to connecting the plate 12 to the vertebra, as illustrated in FIG. 6. The exemplary laminoplasty system also includes an instrument 16 for holding one of the bone plates, and if a bone graft is employed, the bone graft connected to the bone plate, as illustrated in FIGS. 7-16.

The set of bone plates 14 may include a plurality of bone plates of varying sizes and shapes. For example, a set of bone plates 14 may include a plurality of bone plates of two types: in-line bone plates 12A-C and offset bone plates 12D-F, as illustrated in FIG. 1. The exemplary in-line plates 12A-C include a plurality of bone screw receiving holes aligned along the central longitudinal axis CA of the bone plate. The exemplary off-set plates 12D-F include a plurality of bone screw receiving holes, at least two of which are off-set from the central longitudinal axis of the bone plate. The exemplary in-line bone plates 12A-C and offset bone plates 12D-F may come in differing lengths in the system 10. During the surgical procedure, the surgeon may select an appropriate length bone plate based on the length of the space between bone segments the bone plate is to connect. The bone plates 12 may be constructed of any biocompatible material suitable for implantation within the human body, including, for example, stainless steel, titanium and titanium alloys, and polymers, including biodegradable polymers. In one exemplary laminoplasty system, the inline bone plates and the offset bone plates are provided in the following differing lengths: 6 mm, 8 mm, 10 mm, 12 mm, 14 mm, 16 mm, and 18 mm.

Figure 2:
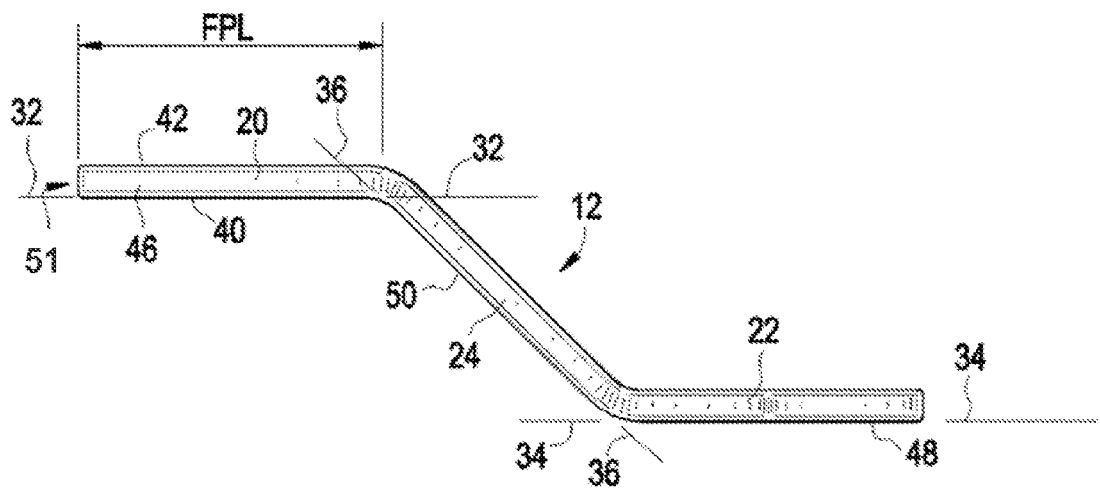
FIG. 2 is a side view of a bone plate of the laminoplasty system of FIG. 1.
Figure 3:
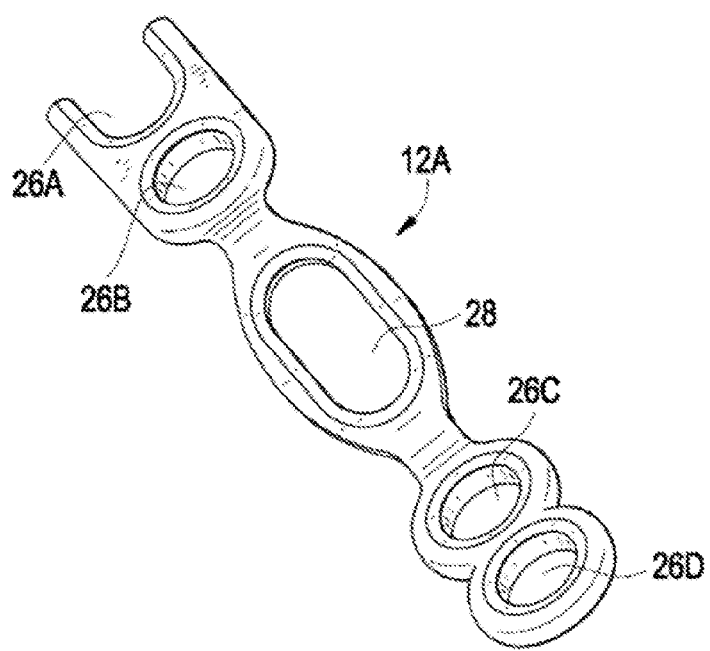
FIG. 3 is a top view of the bone plate of FIG. 2.
Figure 4:
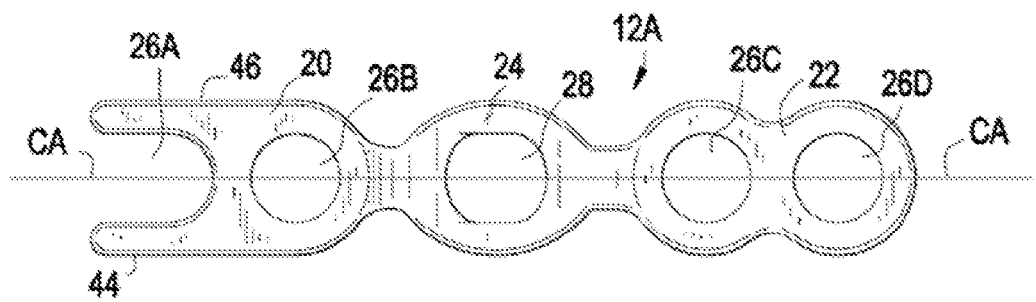
FIG. 4 is a perspective view of the bone plate of FIG. 2.
Figure 5:
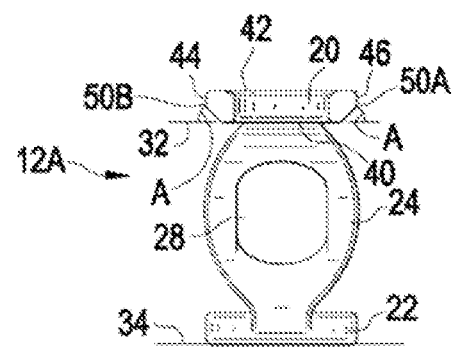
FIG. 5 is a front view of the bone plate of FIG. 2.

Referring to FIGS. 2-6, the exemplary bone plates 12, including bone plates 12A-12D, may include a first plate segment for connecting to a first bone segment, such as the lamina of a vertebra, a second plate segment for connecting to a second bone segment, such as the lateral mass of the vertebra, and a central plate segment for holding a bone graft positioned between the first and second bone segments if a bone graft is employed. Referring to FIGS. 2-4, for example, exemplary in-line bone plate 12A includes a first plate segment 20, a second plate segment 22, and a central plate segment 24 interposed between the first plate segment 20 and the second plate segment 22. The first plate segment 20 may include one or more bone anchor receiving holes. In the exemplary embodiment, for example, the first plate segment 20 includes a first bone anchor receiving hole 26A in the form of an open ended slot and an enclosed, generally circular second bone anchor receiving hole 26B. The second plate segment 22 may include one or more bone anchor receiving holes. In the exemplary embodiment, for example, the second plate segment 22 includes a third bone anchor receiving hole 26C and a fourth bone anchor receiving hole 26D. In the in-line bone plates 12A-C, the first, second, third and fourth bone anchor receiving holes 26A-D are aligned along the central longitudinal axis CA of the bone plate. The central plate segment 24 may include one or more graft openings for receiving an anchor 30 to connect to one of the bone grafts 14. In the exemplary bone plate 12A, for example, the central plate segment 24 includes an elongated, closed slot 28.

The off-set plates 12D-12F of the system 10 may have configuration analogous to that of the in-line plates 12A-12C except the second segment of the off-set plates includes two off-set bone anchor receiving holes 26E, 26F that are positioned off-set from the central longitudinal axis of the bone plate.

The first plate segment 20 includes a planar, distal first bone engaging surface 40, a proximal surface 42, and a first side wall 44 and a second side wall 46 connected by the distal first bone engaging surface 40 and by the proximal surface 42. The second plate segment 22 includes a distal second bone engaging surface 48 and the central plate segment includes a distal third surface 50. The bone plates 12 of the exemplary system 10 may have a geometry to facilitate connection to the lamina of a vertebra at one end, e.g., at the first plate segment, and connection to the lateral mass of the vertebra at the other end, e.g. at the second plate segment. Referring to FIG. 2, for example, the first bone engaging surface 40 of the first plate segment 20 and the second bone engaging surface 48 of the second plate segment 22 of the exemplary bone plate 12 lie in separate, approximately parallel planes, e.g., first plane 32 and second plane 34, respectively, and the distal third surface 50 of the central plate segment 24 connects the first bone engaging surface 40 and the second bone engaging surface 48 and lies in a plane, e.g., third plane 36 that intersects the parallel planes 32 and 34. The first plate segment 20 includes a first plate length FPL extending from a first end 51 to the junction with the central plate segment 24. The first side wall 44 and the second side wall 46 of the exemplary plate 12A each include an angled section 50A, 50B extending from the first distal bone engaging surface 40 toward the proximal surface 42 of the first plate segment 20. In the exemplary plate 12A, the angled sections 50A, 50B are angled away from each other and are oriented at an angle A relative to the first plane 32 that is less than 90°.

A bone graft 14 may be connected to the laminoplasty plate 12A using an instrument that holds the bone graft 14 relative to the plate during insertion of the anchor 30. An exemplary instrument is described in commonly owned, co-pending U.S. patent application Ser. No. 12/609,260, filed Oct. 30, 2009, which is incorporated herein by reference.

Referring to FIG. 7-15, an exemplary instrument 16 for holding one of the plurality of bone plates 12 includes a first arm 62 and a second arm 64 connected to and adjustable relative to the first arm 62. The first arm 62 has a proximal end 66 and a distal end 68. The exemplary instrument 16 includes a first connection tip 70 at the distal end 68 of the first arm 62. The second arm 64 has a proximal end 72 and a distal end 74 and the exemplary instrument 16 includes a second connection tip 76 at the distal end 74 of the second arm 64. The first connection tip 70 of the instrument 16 is configured to connect to one of the side walls of the first plate segment 20 of one of the bone plates 12 of the system 10, e.g., the first side wall 44 or the second side wall 46 of the first plate segment 12A. The second connection tip 76 configured to connect to the other side wall of the first plate segment 20 of the bone plate, e.g., the first side wall 44 or the second side wall 46. The first arm 62 and the second arm 64 being adjustable between a space apart position in which the first connection tip 70 and the second connection tip 76 are spaced apart from each other to facilitate placement of the first plate segment 20 between the first connection tip 70 and the second connection tip 76 and an engaged position in which the first connection tip 70 and the second tip 76 are connected to the first plate segment 20.

The first connection tip 70 and the second connection tip 76 may have a geometry to facilitate placement of a bone plate directly against a bone segment. In the exemplary instrument 16, for example, the first connection tip 70 has a planar distal surface 80 and the second connection tip 76 has a planar distal surface 82. The planar distal surface 80 of the first connection tip 70, the planar distal surface 82 of the second connection tip 76, and the first bone engaging surface 40 of the first plate segment 20 are co-planar when the first connection tip 70 and the second connection tip 76 are connected to side walls of the first plate segment 20. This co-planar configuration allows the first bone engaging surface 40 to be placed directly against a bone segment, e.g., a vertebra, without a portion of the instrument interposed between the plate and the bone and, in laminoplasty procedures, without a portion of the instrument extending into the spinal canal.

The first connection tip 70 and the second connection tip 76 may have length sufficient to engage a sufficient length of the side walls of a bone plate to provide a stable connection during manipulation and anchoring of the bone plate. For example, the first connection tip 70 of the exemplary instrument may extend from a first junction 84 with the distal end 68 of the first arm 62 to a free end 86 of the first connection tip 70. The first connection tip 70 may have a first tip length TL1 extending from the free end 86 to the first junction 84. The second connection tip 76 may extend from a second junction 88 with the distal end 74 of second arm 64 to a free end 90 and the second connection tip 76 may have a second tip length TL2 extending from the free end 90 to the second junction 88. In the exemplary instrument 16, the first tip length TL1 may be approximately equal to the second tip length TL2 and the first tip length TL1 and the second tip length TL2 may be greater than or approximately equal to the first plate segment length FPL. In alternative embodiments, the first tip length TL1 and the second tip length TL2 may have length less than the length of the first plate length or the plate length of the selected bone plate.

Figure 11:
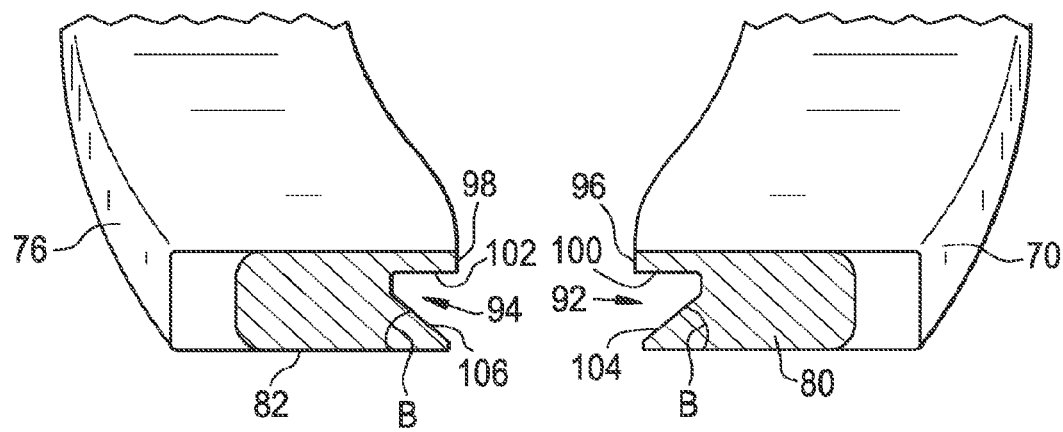
FIG. 11 is a cross sectional view of the connection tips of the instrument of FIG. 7, illustrating the connections tips without a bone plate positioned therebetween.
Figure 14:
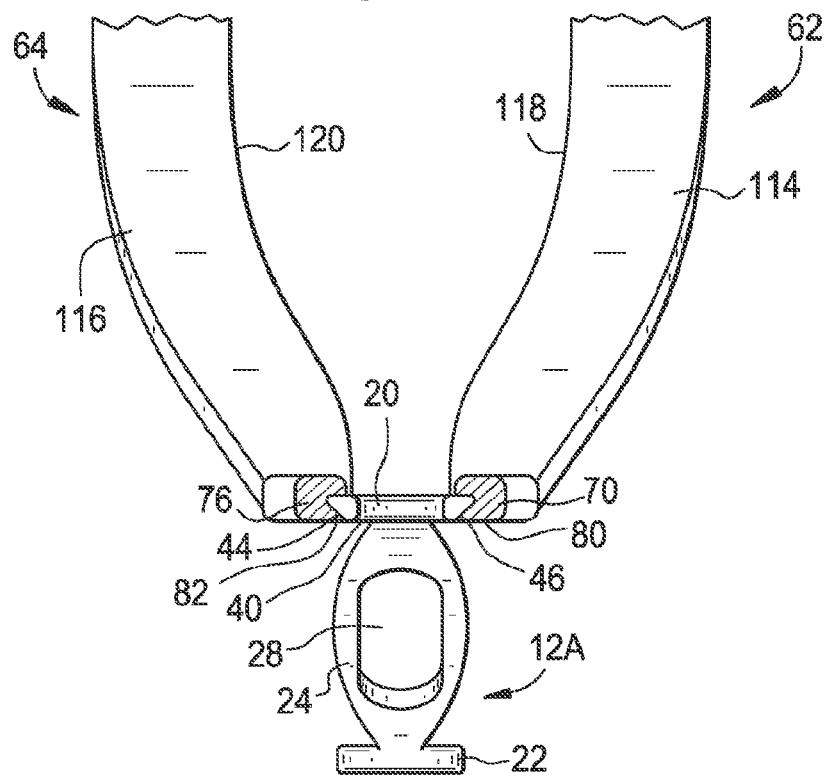
FIG. 14 is a cross sectional view of the distal end of the instrument of FIG. 12, FIGS. 15 and 16 are perspective views of a laminoplasty procedure, illustrating a bone plate being positioned against a vertebra by the instrument of FIG. 7.

Referring to FIGS. 11 and 14, the first connection tip 70 and/or the second connection tip 76 may have a feature to facilitate connection of the connection tips to the selected bone plate. In the exemplary embodiment, for example, the first connection tip 70 has a first groove 92 for receiving the first side wall 44 (or second wall 46) of a bone plate 12A upon connection with the first plate segment 20 of the bone plate 12A. The first groove 92 may extend along at least a portion of the first tip length TL1 and, in the exemplary instrument 16, may extend along the entirety of the first tip length TL1 from the free end 86 to the first junction 84. The second connection tip 76 may have a second groove 94 for receiving the second side wall 46 (or the first side wall 44) upon connection of the second connection tip 76 with the first plate segment 20. The second groove 94 may extend along at least a portion of the second tip length TL2 and, in the exemplary instrument 16, may extend along the entirety of the second tip length TL2 from the free end 90 to the first junction 88. The first groove 92 may be formed in a first inner side wall 96 of the first connection tip 70 and may be open along the first inner side wall 96 to receive the first side wall 44 of the first plate segment 20. The second groove 94 may be formed in a second inner side wall 98 of the second connection tip 76 and may be open along the second inner side wall 98 to receive the second side wall 46 of the first plate segment 20. As the first inner side wall 96 and the second inner wall 98 face each other when engaging a bone plate, the opening in the first groove 92 and the opening in the second groove 94 face each other.

The first groove 92 and the second groove 94 may have a shape that is complementary to the shape of the bone plate received by the grooves. In the exemplary instrument, for example, the first groove 92 has a shape that is complementary in shape to the first and second walls 44, 46 of the first plate segment 20. The first groove 92 may have a distal facing, planar top surface 100 for engaging the proximal surface 42 of the first plate segment 20 and the second groove 94 has a distal facing, planar top surface 102 for engaging the proximal surface 42 of the first plate segment 20. The first groove 92 may have an angled side wall 104 that extends from the planar distal surface 80 of the first connection tip 72 and is oriented at an angle B relative to the distal bone engaging surface 80. The second groove 94 may have an angled side wall 106 that extends from the planar distal surface 82 of the second connection tip 76 and is oriented at the angle B relative to the distal bone engaging surface 82. In the exemplary instrument 16, the angle B is approximately equal to the angle A of the angled sections 50A, 50B of the first and second side walls 44, 46, respectively.

Continuing to refer to FIGS. 7-15, the first arm 62 is pivotally connected to the second arm 64 to provide for pivotal adjustment of the first arm 62 and the second arm 64 the spaced apart position and the engaged position. The proximal end 66 of the first arm 62 and the proximal end 72 of the second arm 64 each may include a handle 108, 110 or the like to facilitate adjustment of the arms. The instrument 16 may also include a locking mechanism, such as ratchet 112, to lock the position of the first arm 62 and the second arm 64.

Figure 9:
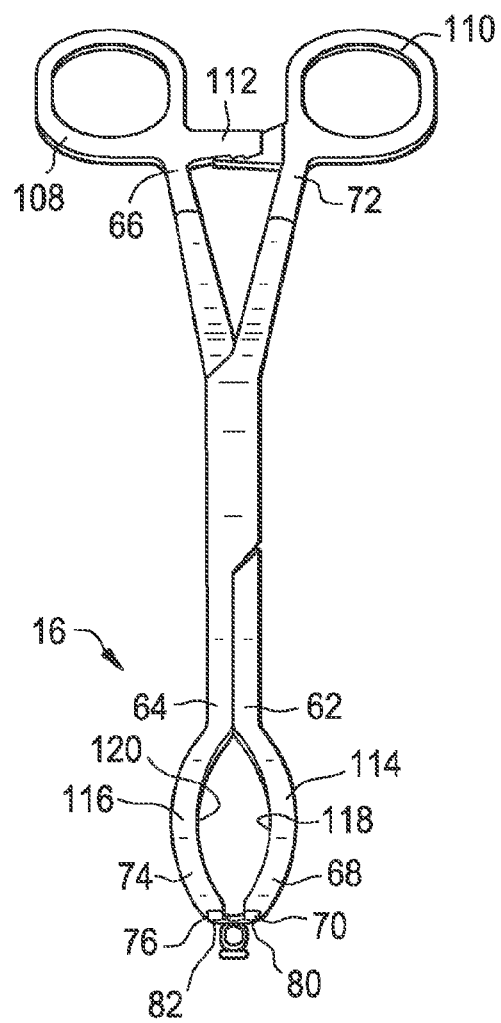
FIG. 9 is a front view of the instrument of FIG. 7.
Figure 10:
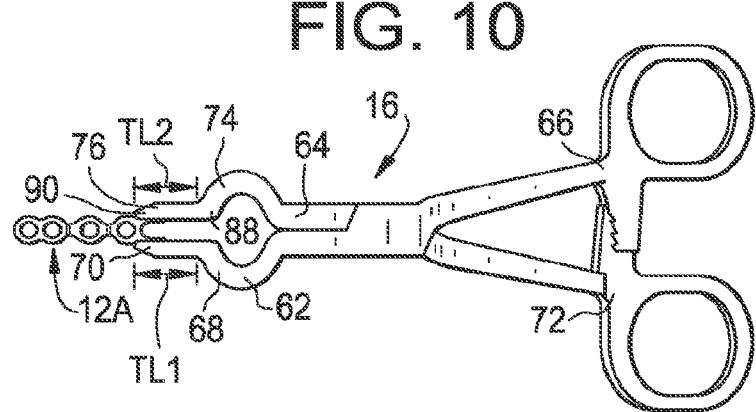
FIG. 10 is a top view of the instrument of FIG. 7.

The first arm 62 and the second arm 64 of the exemplary instrument may be configured to facilitate placement of additional instruments, such as a drill 150 or a screwdriver, and implants, such as bone anchors, to the bone plate connected to the connection tips 70, 76 of the instrument. Referring to FIG. 9, for example, the first arm 62 may include an arcuate segment 114 extending proximally from the first connection tip 70 and a second arcuate segment 116 extending proximally from the second distal connection tip 76. The first arcuate segment 114 includes a first concave inner side wall 118 and the second arcuate segment 116 includes a second concave inner side wall 120 that faces the first concave inner side wall 118 and thereby provides increased space between the first arm 62 and the second arm 64 to access the bone plate connected to the instrument 16 and to provide increased visibility of the anatomy in proximity to the bone plate. The first arcuate segment 114 may be oriented at an angle C of greater than 90° relative to the first connection tip 70 and the second arcuate segment 114 may be oriented at an angle greater than 90° relative to the second connection tip 76, as illustrated in FIG. 8.

Figure 12:
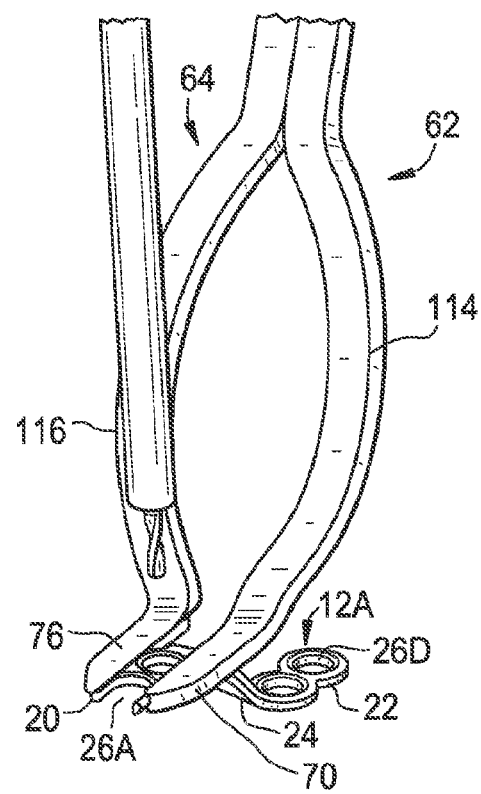
FIG. 12 is a perspective view of the distal end of the instrument of FIG. 7, illustrating the instrument connected to a bone plate in an alternate orientation.
Figure 13:
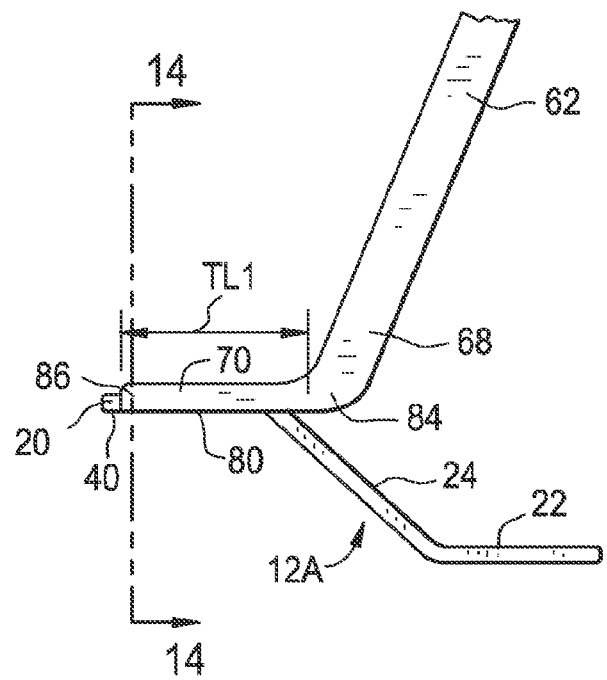
FIG. 13 is a side view of the distal end of the instrument of FIG. 12.

In use, the exemplary instrument 16 may be connected to the first plate segment 20 of the exemplary bone plate 12A by engaging the first connection tip 70 to one of the sidewall of the first plate segment 20 and by engaging the second connection tip 76 to the other sidewall of the first plate segment 20. The first plate segment 20 may be connected to the instrument 16 in one of two orientations: (1) first connection tip 70 engaging first side wall 44 and the second connection tip 76 engaging the second side wall 46, as illustrated in FIGS. 7-10 and 15-16, and (2) first connection tip 70 engaging second side wall 46 and the second connection tip 76 engaging the first side wall 44, as illustrated in FIGS. 12-14. In both orientations, the planar distal surface 80 of the first connection tip 70, the planar distal surface 82 of the second connection tip 76, and the first bone engaging surface 40 of the first plate segment 20 are co-planar when the first connection tip 70 and the second connection tip 76 are connected to side walls of the first plate segment 20.

Figure 15:
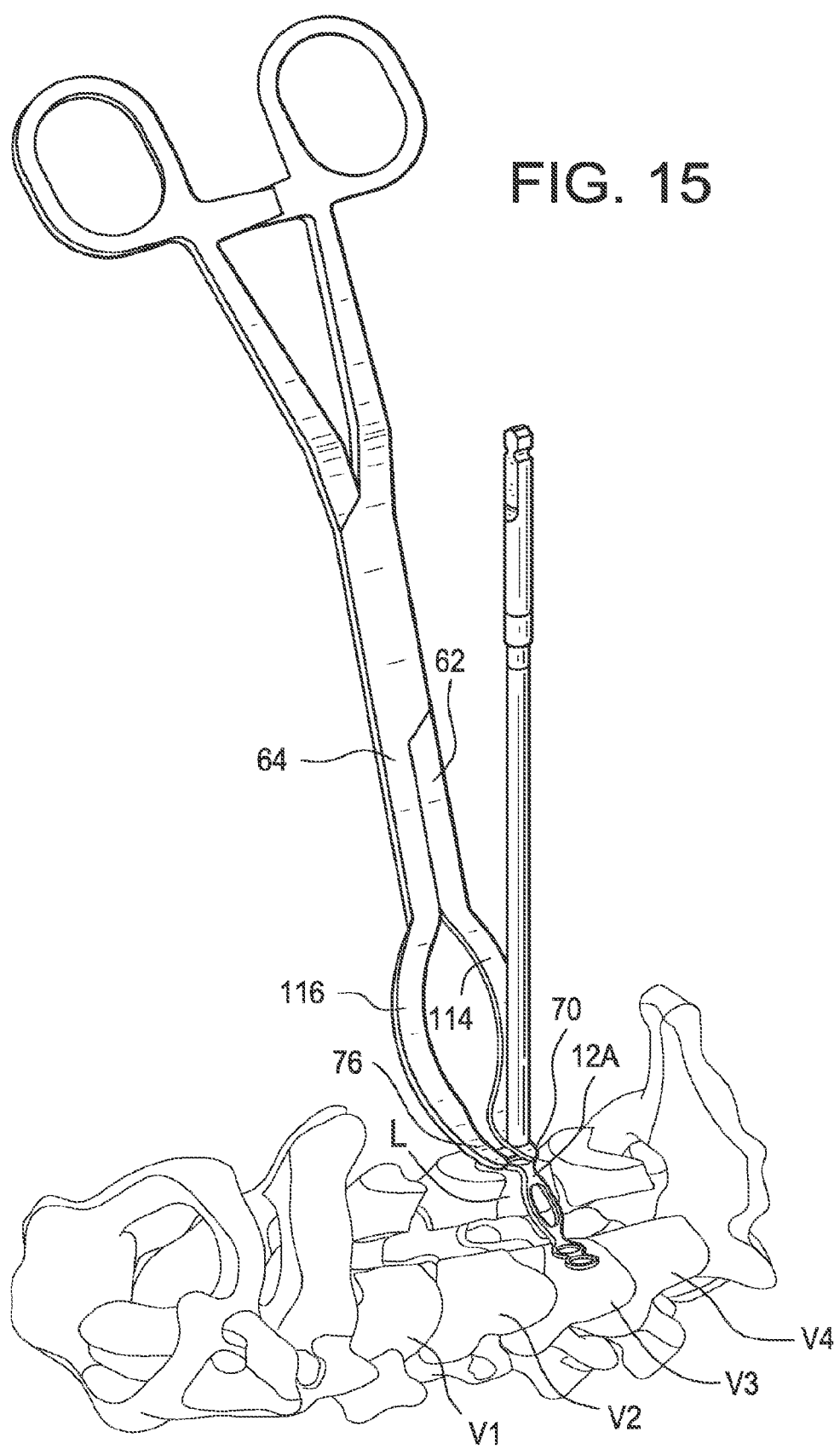
Figure 16:
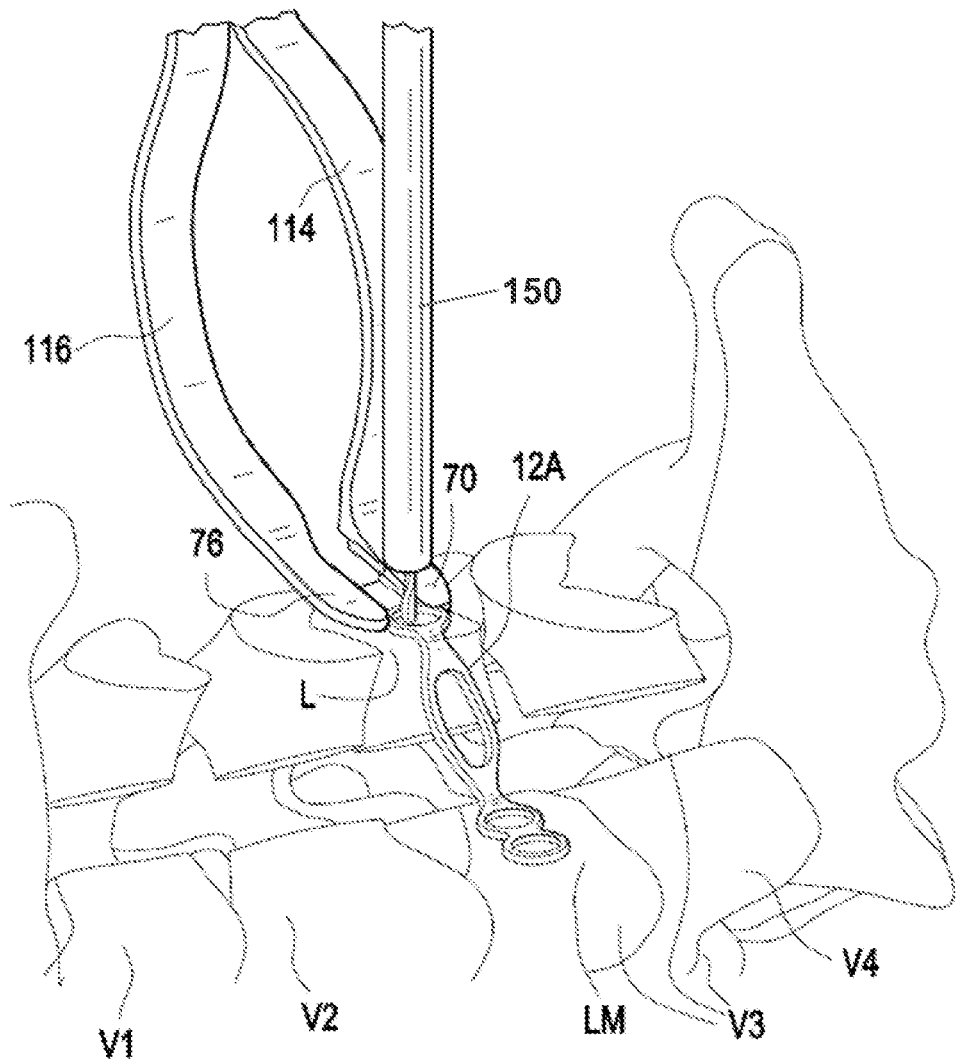

In a laminoplasty procedure, the instrument 16 may be used to manipulate a bone plate, such as plate 12A, into position relative to a vertebra and hold the plate in position while bone anchors are implanted to secure the plate to the vertebra. FIGS. 15 and 16 illustrate an open door laminoplasty procedure to alleviate spinal cord compression by expanding the spinal canal by displacing the lamina of multiple vertebrae that surround the spinal cord. In the illustrated procedure, the lamina of a plurality of adjacent vertebra V1-V4 are completely cut on one side of the spine and on the contra-lateral lamina of each vertebra, a partial cut of the other lamina is made to create a flexible hinge in the bone. This bridge of lamina bone is then levered open about the hinge to expand the spinal canal. Bone plate 12A is manipulated using the instrument 16 to position the first plate segment 20 against the lamina L of the vertebra V3 and to position the second plate segment 22 against the lateral mass LM of the vertebra V3. Once positioned, a drill 150 may be used to drill holes in the lamina and lateral mass for receiving bone anchors. With the instrument 16 holding the bone plate 12A in position, the drill may be positioned through the bone anchor receiving holes 26A-D to drill the requisite holes. With the instrument 16 continuing to hold the bone plate 12A in position, bone anchors may then be positioned through the bone anchor receiving holes 26A-D to anchor the bone plate 12A. Instrument 16 may then be disconnected from the first plate segment 20 by separating the first connection tip 70 and the second connection tip 76.

Figure 17:
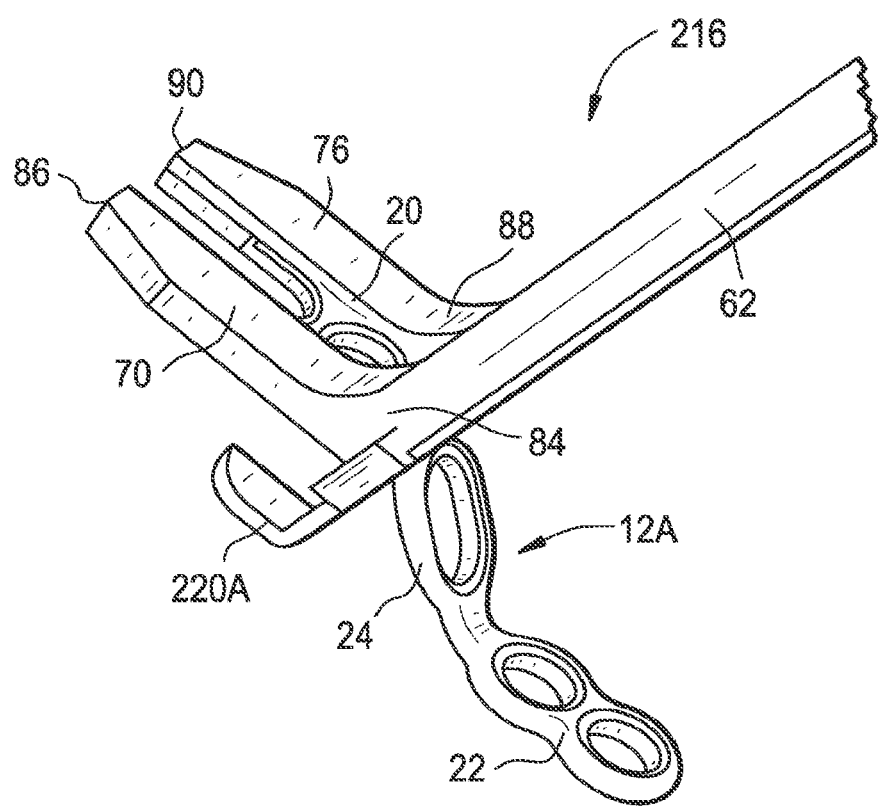
FIG. 17 is a perspective view of an another exemplary embodiment of an instrument for holding a bone plate, illustrating the distal end of the instrument holding a bone plate.
Figure 18:
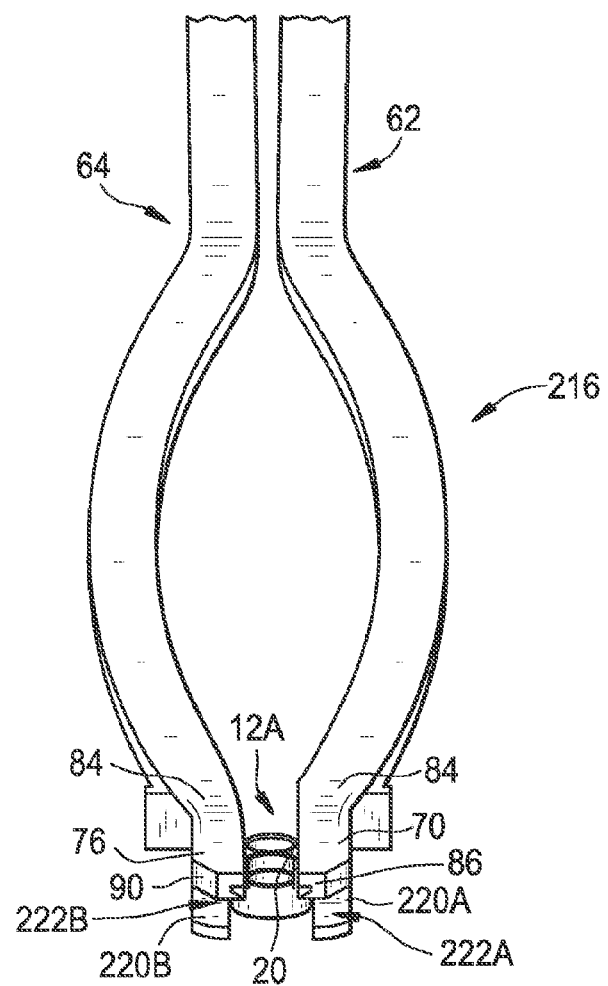
FIG. 18 is a front view of the distal end of the instrument of FIG. 17, illustrating the distal end of the instrument holding a bone plate.
Figure 19:
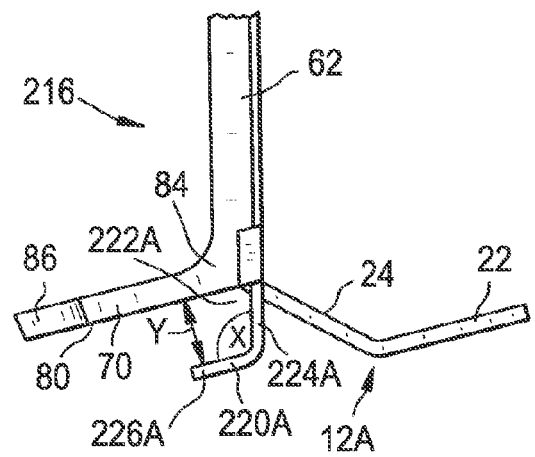
FIG. 19 is a side view of the distal end of the instrument of FIG. 17, illustrating the distal end of the instrument holding a bone plate.
Figure 20:
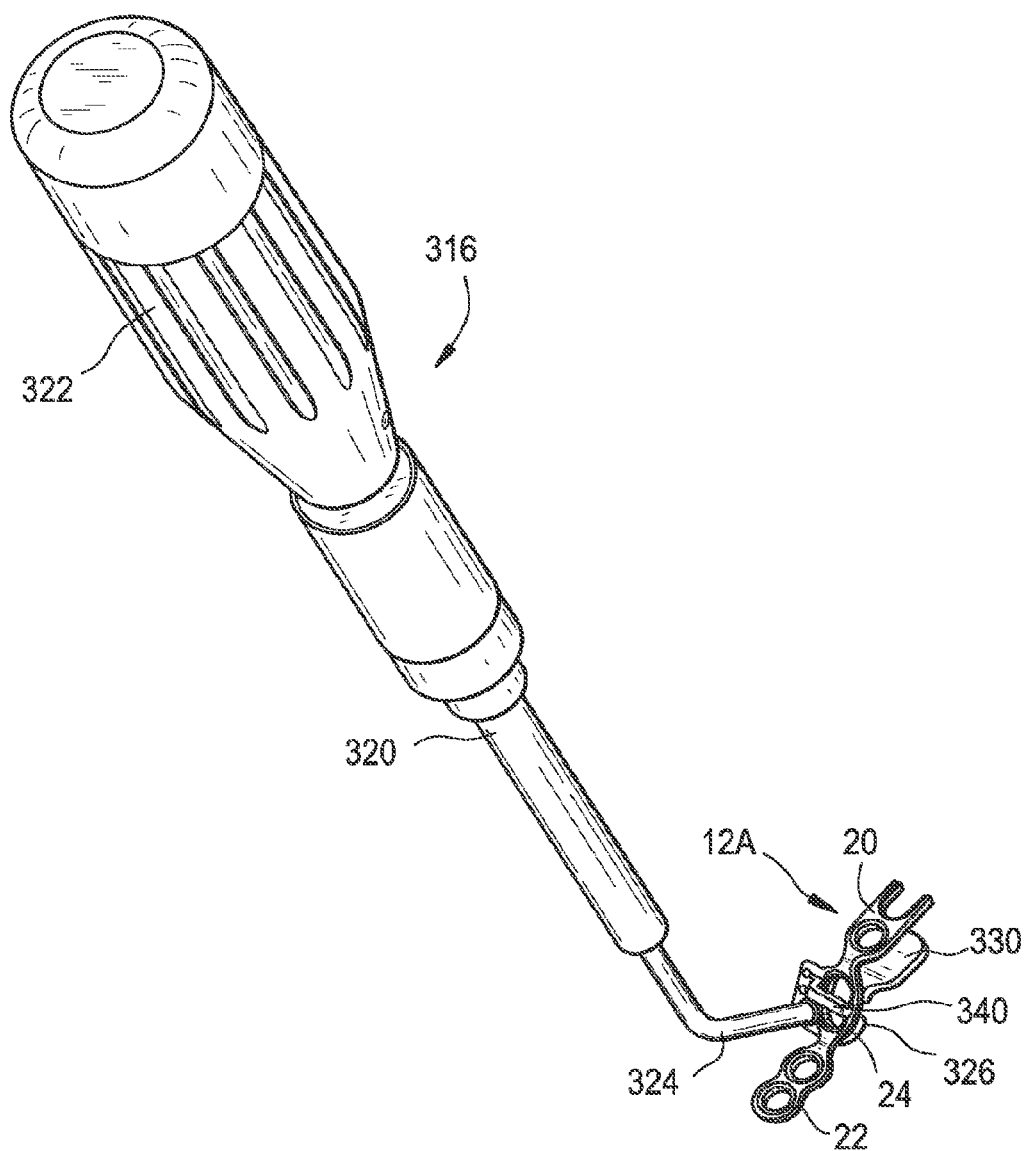
FIG. 20 is a perspective view of an another exemplary embodiment of an instrument for holding a bone plate, illustrating the instrument holding a bone plate.
Figure 21:
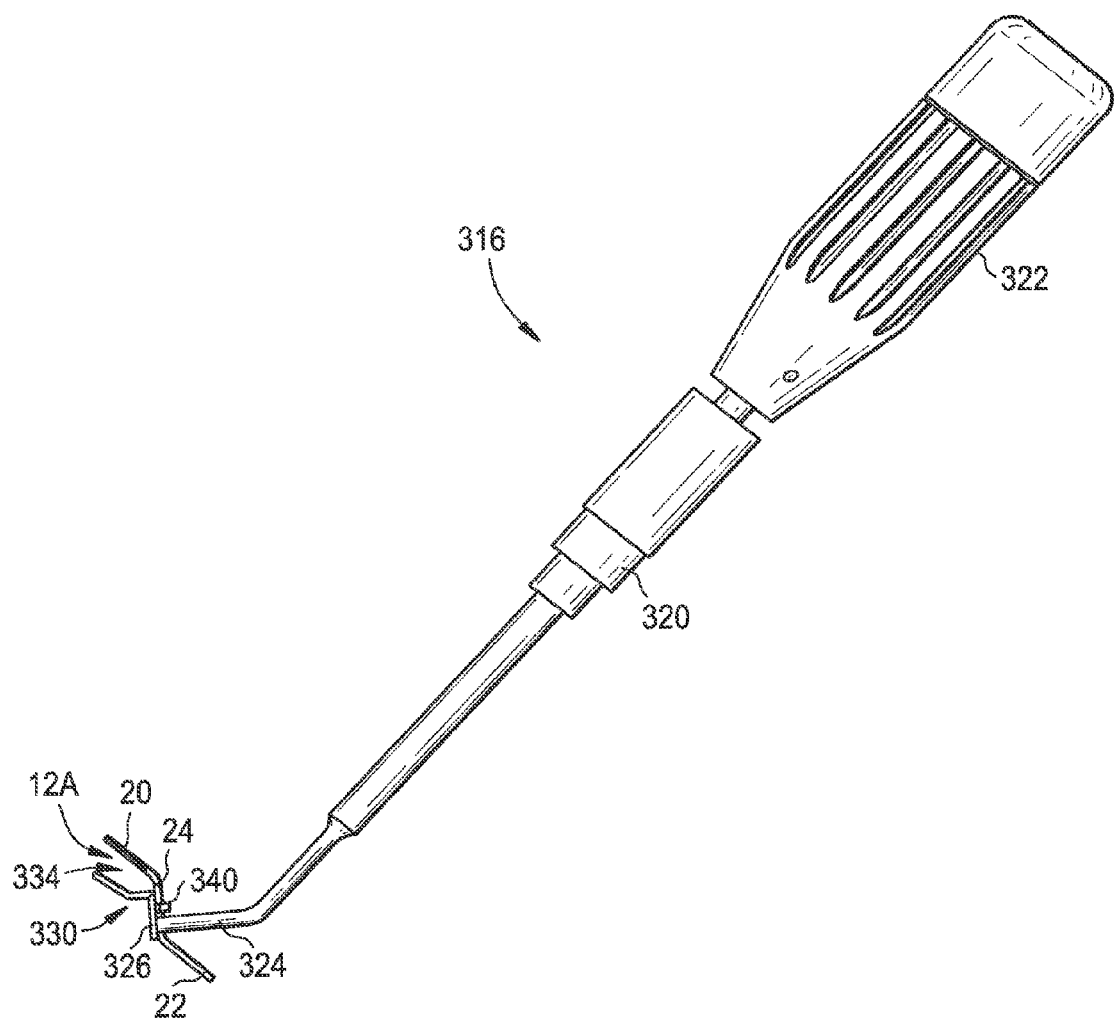
FIG. 21 is a side view of the instrument of FIG. 20, illustrating the instrument holding a bone plate.
Figure 22:
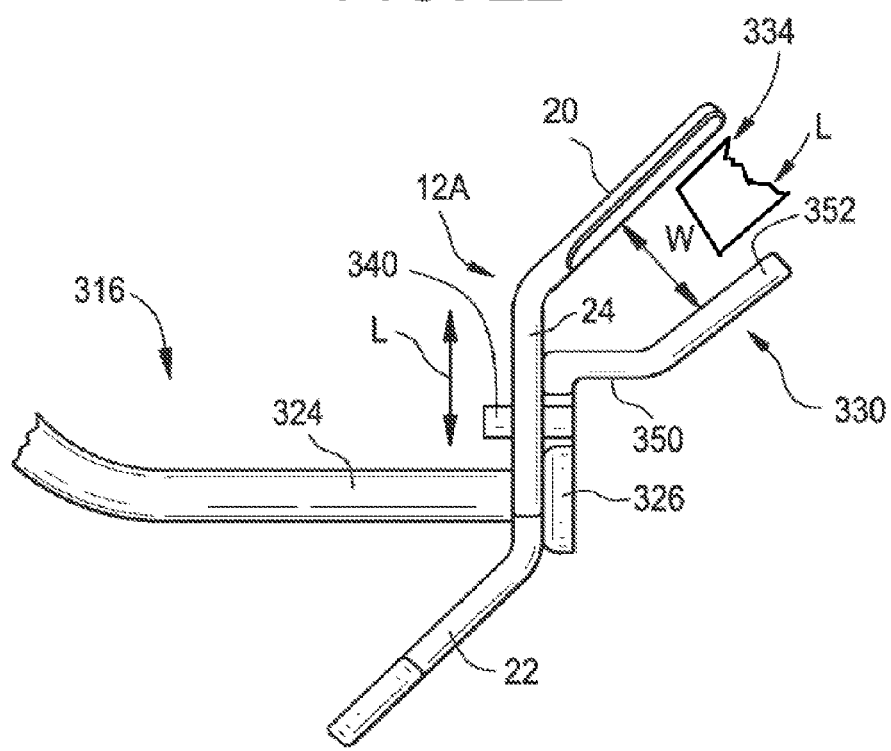
FIG. 22 is a side view of the distal end of the instrument of FIG. 20, illustrating the instrument holding a bone plate.
Figure 23:
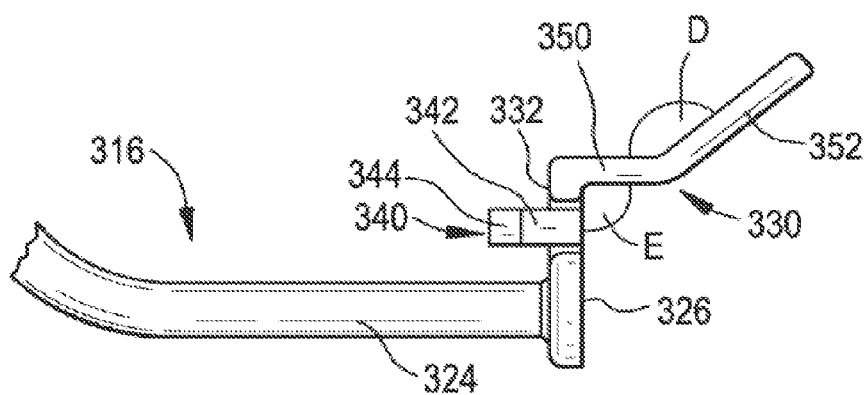
FIG. 23 is a side view of the distal end of the instrument of FIG. 20, FIGS. 24A-C are perspective views of the distal end of the instrument of FIG. 20, illustrating a bone plate in selected positions relative to the plate holding member of the instrument.

FIGS. 17-19 illustrate another exemplary embodiment of an instrument 216 for holding one of the plurality of bone plates 12. The exemplary instrument 216 may be similar in construction to the exemplary instrument 16 described above. The exemplary instrument 216 further includes at least one stabilizing member connected to either or both the first connection tip 70 or the second connection tip 76. In the exemplary embodiment, a first stabilizer member 220A is connected to the first connection tip 70 and a second stabilizer member 220B is connected to the second connection tip 76. Each stabilizing member 220A, 220B is distally spaced apart from the respective connection tip to form an opening 222A, 222B for receiving a portion of bone between the connection tip and the stabilizing member. The stabilizing members 220A, 220B facilitate stabilization of the bone positioned within the spaces 222A, 222B during procedures on the bone including, for example, anchoring the bone plate to the bone or manipulating the bone to a new position or orientation.

In the exemplary embodiment, the stabilizing members 220A, 220B are configured such that the respective openings 222A, 222B are open at the free ends 86, 90 of the first connection tip 70 and the second connection tip 76, respectively. Such a configuration permits bone to be positioned within the openings 222A, 222B from the free ends of the connection tips. For example, the first stabilizing member 220A connects to first connection tip 70 proximate the first junction 84. The first stabilizing member 220A includes a connection segment 224A connected to the first connection tip 70 proximate the first junction 84 and a second segment 226A connected to the connection segment 224A. The second segment 226A may be oriented at an angle X to the connection segment 224A and may extend from the connection segment 224A toward the free end 86 of the first connection tip 70. The angle X may be selected to orient the second segment 226A generally parallel to the distal surface 80 of the first connection member 70. For example, the angle X may be an acute angle. The distance Y between the distal surface 80 of the first connection tip 70 and the second segment 226A may be selected based on the size of the bone to be positioned within the opening 222A. For laminoplasty procedures in which the opening 222A is designed to receive a portion of the cut lamina, for example, the distance Y may approximate the width of the lamina. Accordingly, for laminoplasty procedures the distance Y may be between approximately 1.5 mm to approximately 12 mm and is preferably between approximately 3 mm and approximately 7 mm. In embodiments in which two stabilizing members are provided, such as the illustrated instrument 216, the second stabilizing member 220B may be configured analogously to the first stabilizing member 220A.

The exemplary instrument 216 may be used in laminoplasty procedures to stabilize the cut lamina during the procedure. For example, the cut lamina may be positioned within the openings 222A, 222B between the distal surface of the first connection member 70 and the second segment 226A of the first stabilizing member 220A and between the distal surface of the second connection member 76 and the second segment of the second stabilizing member 220B. The cut lamina may be positioned within the openings 222A, 222B with the bone plate, for example bone plate 12A, connected to the instrument 216 or without the bone plate connected to the instrument 216. With the bone plate connected to the instrument 216, the instrument may be used to stabilize the cut lamina as the bone plate is anchored to the lamina and lateral mass of the vertebra and during pivoting of the cut lamina about the hinge in the contra-lateral lamina. Without the bone plate connected to the instrument, the instrument may be used to stabilize the cut lamina during pivoting of the cut lamina about the hinge in the contra-lateral lamina or during other parts of the procedure.

FIGS. 20-24C illustrate an alternative embodiment of an instrument for holding a bone plate and stabilizing bone during surgical procedures. The exemplary instrument 316 includes a shaft 320 having a proximal handle 322 and a distal end 324, a plate holding member 326 connected to the distal end 324 of the shaft 320, and a stabilizing member 330 connected to the plate holding member 326. The plate holding member 326 defines a proximal surface 332 for receiving a first plate segment of the bone plate, for example, central plate segment 24 of bone plate 12A. The stabilizing member 330 may be distally spaced apart from the plate holding member 326 to form an opening 334 for receiving a portion of bone between the stabilizing member 330 and a second plate segment of the bone plate, for example the first plate segment 20 of bone plate 12A, when the first plate segment (e.g. central plate segment 24) is positioned on the proximal surface 332 of the plate holding member 326.

The proximal surface 332 of the plate holding member 326 may have a shape that is complementary to the distal surface of the bone plate to facilitate holding of the plate. For example, the proximal surface 332 of the plate holding member 326 of the exemplary embodiment is generally planar to engage the generally planar distal surface of the central plate segment 24 of the bone plate 12A.

The instrument 316 may include a retaining element 340 for retaining the first plate segment (e.g., central plate segment 24) against the proximal surface 332 of the plate holding member 326. The retaining element 340 permits the first plate segment (e.g., central plate segment 24) to be positioned at selected positions along the axial length of the plate holding member 326, as illustrated by the arrow L, and in a direction parallel to the plane defined by the proximal surface 332. The retaining element 340 may be connected to the plate holding member 326 by a first section 342 extending proximally from the proximal surface 332 of the plate holding member 326. The retaining element 340 may include a second section 344 connected to the first section 342. The second section 344 may be oriented approximately parallel to and spaced apart from the proximal surface 332 of the plate holding member 326 to define a space for receiving the first plate segment (e.g., central plate segment 24). The height of the space, i.e., the distance between the second section 344 and the proximal surface 332 of the plate holding member 326, is preferably selected to retain the plate relative to the instrument 316 as the plate is manipulated during a surgical procedure. The height of the space may be less than or equal to the thickness of the first plate segment (e.g., central plate segment 24).

The retaining element 340 may be pivotally connected to the plate holding member 326 such that the second section 344 may be pivoted from a parallel orientation relative to the proximal surface 332 of the plate holding member 326 to permit insertion of the first plate segment (e.g., central plate segment 24) between the second section 344 and the proximal surface 332 of the plate holding member 326. The second section 344 may be biased to the parallel orientation to facilitate retention of the plate.

The stabilizing member 330 may include a connection segment 350 connected to the plate holding member 326 and a second segment 352 connected to the connection segment 350. The second segment 352 may be oriented at an angle to the connection segment 350 and may extend from an end of the plate holding member 326. The second segment 352 may be angled relative to the connection member 350 to provide an opening 334 sized and shaped to receive selected bone. The size and shape of the opening 334 is defined by the angle D of the second segment 352 relative to the connection segment 350, the angle E of the connection segment 350 relative to the plate holding member, the shape of the bone plate, and the position of the bone plate relative to the plate holding member 326, as discussed in more detail below. Depending on the desired size and shape of the opening 334, the connection segment 350 may be oriented at an acute angle relative the plate holding member 326 or may be oriented at an obtuse angle relative the plate holding member 326 and the second segment 352 may be oriented at an acute angle relative the connection segment 350 or may be oriented at an obtuse angle relative the connection segment 350. For the exemplary instrument 316, which is designed to stabilize a portion of the cut lamina during a laminoplasty procedure, the angle D is an obtuse angle and the angle E is approximately 90°. In this configuration, when the central plate segment 24 of the bone plate 12A is positioned against the proximal surface 332 of the plate holding member 326, the second segment 352 of the stabilizing member 330 is oriented generally parallel to the plate segment 20 of the bone 12A.

Figure 24A:
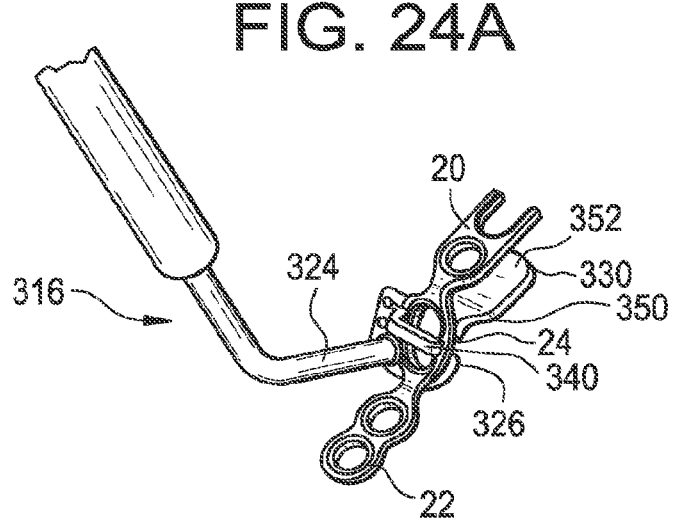
Figure 24B:
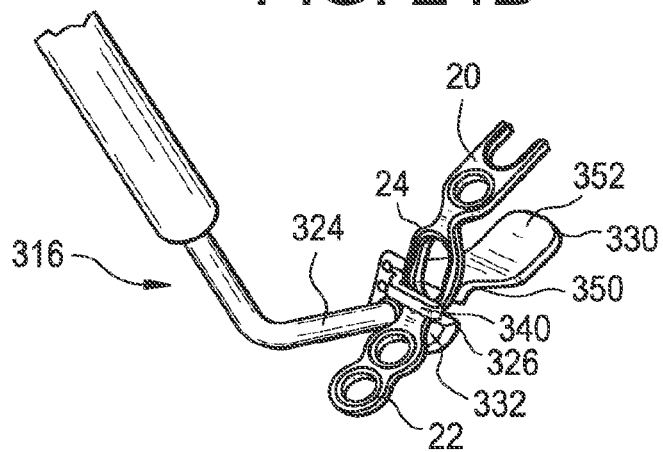
Figure 24C:
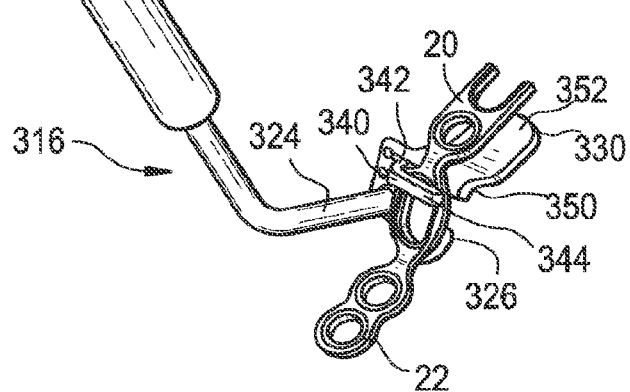

By adjusting the position of the central plate segment 24 along the axial length of the plate holding member 326, i.e., along arrow L, the distance W between the plate segment 20 and the second segment 352 of the stabilizing member 330 may be varied. The distance W between the plate segment 20 and the second segment 352 of the stabilizing member 330 may be selected based on the size of the bone to be positioned within the opening 334. For laminoplasty procedures in which the opening 334 is designed to receive a portion of the cut lamina, for example, the distance W may approximate the width of the lamina. Accordingly, for laminoplasty procedures the distance W may be adjusted between approximately 1.5 mm and approximately 12 mm. FIG. 24A illustrates a central position of the central plate segment 24 of the bone plate 12A relative to the retaining member 340, which corresponds to the approximate mid-point within the range for distance W. By adjusting the central plate segment 24 such that the retaining member 340 is proximate plate segment 22, as illustrated in FIG. 24B, the distance W is increased. By adjusting the central plate segment 24 such that the retaining member 340 is proximate plate segment 20, as illustrated in FIG. 24C, the distance W is decreased.

As with the instrument 216, the exemplary instrument 316 may be used in laminoplasty procedures to stabilize the cut lamina during the procedure. For example, the cut lamina may be positioned within the opening 334 between the plate segment 20 and the second segment 352 of the stabilizing member 330. The cut lamina may be positioned within the opening 334 with a bone plate, for example bone plate 12A, connected to the instrument 316. By adjusting the central plate segment 24 relative to the plate holding member 326 along arrow L the distance W between the plate segment 20 of the bone plate 12A and the stabilizing member 330 can be adjusted to correspond to the thickness of the cut lamina. For example, the central plate segment 24 may be adjusted in a first direction toward the stabilizing member 330 to increase the distance between the plate segment 20 of the bone plate 12A and the stabilizing member 330. Alternatively, for example, the central plate segment 24 may be adjusted in a second direction way from the stabilizing member 330 to decrease the distance between the plate segment 20 of the bone plate 12A and the stabilizing member 330. In one exemplary procedure, the central plate segment 24 may be positioned to provide for the maximum distance between the plate segment 20 of the bone plate 12A and the stabilizing member 330, as illustrated in FIG. 24B. The cut lamina may positioned within the opening 334 between the plate segment 20 of the bone plate 12A and the stabilizing member 330 and the central plate segment 24 may be adjusted in the second direction, away from the stabilizing member 330, to adjust the distance W to correspond to the thickness of the cut lamina.

FIGS. 25 and 26 illustrate an alternative embodiment of the instrument 316 in which the retaining member 340 is fixed relative to the plate holding member 326 rather than being pivotally connected to the plate holding member 326. In this exemplary embodiment, the distance between the second section 344 of the retaining member 340 and the proximal surface 332 of the plate holding member 326 is selected to provide for a friction fit of the bone plate to the plate holding member 326. For example, the distance between the second section 344 and the proximal surface 326 may be equal to or less than the thickness of the central plate segment 24 of the bone plate 12A.

While the present instruments has been described in connection with exemplary laminoplasty plate 12A and the other laminoplasty plates of the system 10, the instruments described may be used with any type of bone plate, including, for example, anterior cervical plates, anterior lumbar plates, trauma plates, and fracture fixation plates.

While the devices and methods of the present invention have been particularly shown and described with reference to the exemplary embodiments thereof, those of ordinary skill in the art will understand that various changes may be made in the form and details herein without departing from the spirit and scope of the present invention. Those of ordinary skill in the art will recognize or be able to ascertain many equivalents to the exemplary embodiments described specifically herein by using no more than routine experimentation. Such equivalents are intended to be encompassed by the scope of the present invention and the appended claims.

The invention claimed is:

1. A method of expanding the spinal canal of a vertebra comprising:
   cutting completely through the first lamina to create a space in the first lamina,
   cutting partially through a second, contra-lateral lamina of the vertebra to create a partial cut in the second lamina,
   connecting a first plate segment of a bone plate to a plate holding member of a plate holding instrument,
   manipulating the plate holding instrument to position the first lamina in a space between a second plate segment of the bone plate and a stabilizing member of the plate holding instrument to thereby stabilize the first lamina,
   pivoting the first lamina about the partial cut in the second lamina to increase the extent of the space in the first lamina,
   connecting the second plate segment to the first lamina, and
   connecting a third plate segment of the bone plate to a portion of the vertebra across the space from the second plate segment such that the first plate segment spans the increased space and the bone plate stabilizes the vertebra.

2. The method of claim 1, wherein the first lamina is stabilized by the plate holding instrument during the pivoting of the first lamina.

3. The method of claim 1, wherein pivoting of the first lamina occurs after connecting the second plate segment to the first lamina.

4. The method of claim 3, wherein the first lamina is stabilized by the plate holding instrument during connecting of the second plate segment to the first lamina.

5. The method of claim 1, further comprising adjusting the first plate segment relative to the plate holding member to change the space between the second plate segment of the bone plate and the stabilizing member to correspond to the thickness of the first lamina.

6. The method of claim 5, further comprising adjusting the first plate segment in a first direction to increase the space between the second plate segment of the bone plate and the stabilizing member.

7. The method of claim 5, further comprising adjusting the first plate segment in a second direction, to decrease the space between the second plate segment of the bone plate and the stabilizing member.

* * * * *